United States Patent [19]
Seki et al.

[11] Patent Number: 5,776,904
[45] Date of Patent: Jul. 7, 1998

[54] DISPERSION PREPARATION

[75] Inventors: Junzo Seki, Hyogo; Hirofumi Yamamoto, Kyoto, both of Japan

[73] Assignee: Nippon Shinyaku Co., Ltd., Japan

[21] Appl. No.: 50,217

[22] PCT Filed: Nov. 15, 1991

[86] PCT No.: PCT/JP91/01564

§ 371 Date: Jun. 3, 1993

§ 102(e) Date: Jun. 3, 1993

[87] PCT Pub. No.: WO92/08467

PCT Pub. Date: May 29, 1992

[30] Foreign Application Priority Data

Nov. 16, 1990 [JP] Japan .................. 2-312057

[51] Int. Cl.$^6$ ........................... A61K 31/70
[52] U.S. Cl. ........................... 514/31; 536/6.5
[58] Field of Search .................. 514/31; 536/6.5

[56] References Cited

U.S. PATENT DOCUMENTS

| | | | |
|---|---|---|---|
| 3,928,570 | 12/1975 | Metzger | 424/118 |
| 4,002,741 | 1/1977 | Kulbakh et al. | 514/31 |
| 4,035,567 | 7/1977 | Sipos | 536/6.5 |
| 4,844,900 | 7/1989 | de Albornoz et al. | 424/501 |
| 5,043,107 | 8/1991 | Adler-Moore et al. | 264/3.6 |

FOREIGN PATENT DOCUMENTS

| | | |
|---|---|---|
| 0147851 | 7/1985 | European Pat. Off. . |
| 8806450 | 9/1988 | WIPO . |
| 9001873 | 3/1990 | WIPO . |

OTHER PUBLICATIONS

Szoka et al. *Antimicrobial Agents And Chemother.*, 31: 421–429 (1987).

Kirsh et al. *J. Infec. Dis.*, 158: 1065–1070 (1988).

*Primary Examiner*—Elli Preselev
*Attorney, Agent, or Firm*—Graham & James LLP

[57] ABSTRACT

Liquid dispersions are produced wherein amphotericin B, the methyl ester thereof, nystatin, trichomycin, primaricin and the like having a particle size of 10 μm or less are dispersed in a suitable solvent such as physiologically acceptable saline. The dispersions are particularly useful for parenteral administration.

16 Claims, No Drawings

DISPERSION PREPARATION

TECHNICAL FIELD

The present invention relates to a dispersion preparation containing amphotericin B.

BACKGROUND ART

Even today, about 30 years after its development, amphotericin B is widely used as an important antifungal agent which may be administered to the entire body and which exhibits reliable effects. However, this substance has a drawback in that it causes serious side effects due to its hemolytic toxicity and nephrotoxicity.

In order to alleviate these side effects, amphotericin B has been administered in the form of a liposome preparation containing phospholipids, a lipid complex preparation, or a fatty emulsion preparation prepared by emulsifying soybean oil with a small amount of a phospholipid (Szoka, P. C. Jr, et al., Antimicrobial Agents and Chemotherapy, 31, 421–429, 1987, hereunder referred to as "Document 1"; Kirsh, R., et al., Journal of Infectious Diseases, 158, 1065–1070, 1988, hereunder referred to as "Document 2"; and Japanese Patent Application Disclosure SHO 63-66123, hereunder referred to as "Document 3", etc.).

Nevertheless, although these various types of liposome preparations, lipid composite preparations and fatty emulsion preparations reduce the hemolytic toxicity of amphotericin B and are successful in reducing acute toxicity, practically no effects have been observed towards reduction of nephrotoxicity, which is the greatest problem in the clinic. In addition, these various types of liposome preparations, lipid composite preparations and fatty emulsion preparations have serious drawbacks both economically, as they use large amounts of high-cost lipids, and in that during their prolonged administration, they add to the influence of other additives to produce hypercholesteremia, fatty liver, etc.

In contrast, dispersion preparations do not require the lipids which cause the above mentioned disadvantages.

Known amphotericin B dispersion preparations include amphotericin B syrups, etc. intended for only oral administration, but the use of large amounts of glycerin, carboxymethyl cellulose, etc. therein as aids, whose crystals easily precipitate upon dilution, leads to many disadvantages including the possibility of toxic effects of those aids in the body. No amphotericin B dispersion preparation for parenteral administration has heretofore existed.

In order to administer amphotericin B at a high concentration, it is more preferable to use amphotericin B dispersed in a dispersion preparation, rather than combined with another ingredient such as a carrier, etc. It is necessary to alleviate the hemolytic toxicity and nephrotoxicity without influencing the pharmacological mechanism (antifungal action) of amphotericin B itself on the molecular level. It is the object of the present invention to provide a solution to these problems.

DISCLOSURE OF THE INVENTION

The present invention is largely characterized by providing an amphotericin B preparation which may be administered intravenously without the use of adjuvants of any kind.

It has been heretofore commonly known in making preparations that preparations for intravenous administration must not contain insolubles (this is specified in Japanese Pharmacopoeia), and in order to administer an effective amount of the hardly soluble amphotericin B as a drug, there has been no method other than using an adjuvant such as a synthetic surfactant, etc. or administering it as an inclusion in a carrier. The method described in Document 1 for its administration as a liposome type or lipid complex also follows this line of thought.

However, it became clear that, in contrast to what has been common knowledge, amphotericin B itself will exist in a permanently stable manner when uniformly dispersed as minute particles in a generally used injectable solvent such as physiological saline, etc., even without the use of any type of adjuvant, and without causing precipitation or aggregation.

We the inventors of the present invention came across this fact in a coincidental manner, and the present invention was completed based thereupon.

The gist of the present invention resides in an in-liquid dispersion preparation itself as one form of a preparation of amphotericin B. Here, "in-liquid" means in-water, and the in-liquid dispersion preparation refers to a preparation in which the main ingredient, amphotericin B itself, is permanently and stably dispersed in water. Here, "permanently" means that there is no change as time progresses, and "dispersed" essentially means a suspended state.

For a dispersion preparation according to the present invention, there is no need for the use of any type of aid for the dispersion. As a result, a dispersion preparation according to the present invention contains substantially no dispersion agent. Here, "substantially" means for the purpose of facilitating the dispersion.

The particle size of a dispersion preparation according to the present invention is 10 μm or less, as described below.

During the production of a dispersion preparation according to the present invention, any of the various methods for production of dispersion preparations may be used which have hitherto been employed. For example, a production method may be used in which a Manton-Gauline pressurized spray type homogenizer, microfluidizer or ultrasonic homogenizer, etc. is used for adequate dispersion or minuteness of crude amphotericin B. If a Manton-Gauline pressurized spray type homogenizer is used, it may be applied at a pressure of about 300–1,000 kg/cm$^2$ for approximately 30–60 minutes. In this manner, adequate dispersion may be achieved for the dispersion preparation according to the present invention described below.

Also, if a microfluidizer is used, an air pressure of about 3–5 kg/cm$^2$ is adequate. If an ultrasonic homogenizer is used, it may be applied at an output of about 50–200 W for about 5 minutes to 2 hours, although this will depend on the manner of use. If it is desired to reduce the size of the dispersion particles, the output may be increased or the time may be prolonged in order to consistently obtain a dispersion preparation according to the present invention having the desired particle size.

Crude amphotericin B may be precrushed with a conventional crusher prior to effecting these wet dispersions.

For a dispersion preparation according to the present invention, the concentration of amphotericin B may be determined depending on the amount needed for the preparation.

If the concentration is 20% or higher for the production of the dispersion preparation according to the present invention then the efficiency of dispersion is known to be lower, and therefore the concentration of amphotericin B is preferred to be 0.005–20% (w/v).

The form and particle size of the dispersion preparation according to the present invention may be easily confirmed using an electron microscope, a light-scattering particle size analyzer, by filtration with a membrane filter, or the like.

It is not apparent whether the particles of the dispersion preparation according to the present invention exist as a crystalline state or an amorphous state. It is not possible to confirm the crystalline structure thereof using a means of analysis such as powder X-ray diffractometry, etc., but with an electron microscope, the presence of particles having a size of approximately 0.005–10 µm can be confirmed A dispersion preparation according to the present invention generally has a particle size of about 10 µm or less. This may be dispersed in a liquid without the use of a dispersing agent. In such a dispersion preparation, particles of approximately 1 µm or smaller do not precipitate even upon centrifugal separation. Particles of approximately 0.2 µm or less do not precipitate even upon ultracentrifugation. A smaller particle size is understood to increase the stability of the dispersion.

During the production of a dispersion preparation according to the present invention, a commonly used, a physiologically acceptable dispersion agent or stabilizer may be added, although they are unnecessary for the purpose of stability of the dispersion of amphotericin B. Available examples thereof include, for example, propylene glycol, glycerine, polyethylene glycol, gelatin, dextran, polyvinylpyrrolidone, carboxymethyl cellulose, methyl cellulose, hydroxypropyl cellulose, sucrose fatty acid esters, polyoxyethylene hydrogenated castor oil, sterols, phospholipids, fatty acids, sugars, etc.

As described below, a dispersion preparation according to the present invention may contain physiologically acceptable additives as desired. For example, additives, aids, etc. which are normally used in injections may be added thereto, including antioxidants, antiseptics, stabilizers, isotonizing agents, buffering agents, etc. The required and optimum amounts of these substances may be varied depending on the object.

A dispersion preparation according to the present invention obtained in the manner described above may, as necessary, be sterilized (for example, sterilization by filtration, high pressure steam sterilization, etc.) and filled in an ampule with nitrogen gas. In addition, a drying procedure involving a conventional method such as lyophilization, spray drying, etc. may be used as necessary. The dried preparation according to the present invention may be reconstituted by the addition of an appropriate solution. The dispersion preparation according to the present invention which is dried in this manner is also included in the present invention.

A dispersion preparation according to the present invention may be administered intravenously to humans or various animals for the treatment or prevention of fungus or virus infections. Or, a dispersion preparation according to the present invention may be administered as necessary in the form of an intraarterial, intramuscular, intraspinal or subcutaneous injection, etc. It may also be prepared and used as an eye drop, nasal drop, oral medicine, inhalant, bladder infusion, external preparation or suppository, etc. In this case as well, a pharmaceutically acceptable additive such as a base, excipient, etc. may be used as an optional ingredient.

The dose of a dispersion preparation according to the present invention will differ depending on the route of administration, the form of the preparation, the symptoms of the patient and the desired purpose, but as a dispersion preparation generally 1–1000 ml per administration is adequate. A dose of amphotericin B of 1–200 mg per administration for adults is generally adequate.

The polyene antifungal antibiotic suitable for incorporation into a dispersion preparation according to the present invention may be, in addition to amphotericin B, a methyl ester of amphotericin B, nystatin, trichomycin, pimaricin, etc.

When an effective dose of a dispersion preparation according to the present invention has been administered, none of the kidney function-damaging properties of amphotericin B were observed, and thus alleviation of the major disadvantage of nephrotoxicity of amphotericin B is accomplished. In addition, the alleviation of nephrotoxicity was completely substantiated by measurement of the amount of the drug which migrated to the kidneys upon administration (Test 3).

In a dispersion preparation according to the present invention, since amphotericin B itself may be present in a liquid, the amount of particles of the preparation is sufficient at, for example, about ½₀₀ of the amount required in methods of the prior art in which amphotericin B is present in a liquid as a result of dissolution in a carrier such as a liposome or fatty emulsion.

Since the amphotericin B itself according to the present invention is present as a fine solid particles, it is resistant to thermal and oxidative decomposition.

According to the present invention, it is possible to considerably increase the value of the use of amphotericin B in the clinic.

The effects of the present invention to overcome the disadvantages of the prior art may be summarized as follows:

1) Considerable alleviation not only of hemolytic toxicity of amphotericin B, but also alleviation of nephrotoxicity which has been a major object of improvement,
2) Improvement in migration to the lesion,
3) Solution to the problem of outbreak of hypercholesteremia and fatty liver due to the lipids which have been conventionally used as additives,
4) Reliable stability during storage, and
5) Lower production costs due to simplification of the production process and no use of expensive additives. These effects have been first achieved with the present invention.

The constituent of the dispersion preparation according to the present invention is essentially only amphotericin B, a drug whose use has been accepted for years in the medical field as a medical therapy, and as it contains absolutely n oadditives whose safety has not been guaranteed, it may be used very safely.

THE BEST MODE FOR CARRYING OUT THE INVENTION

A more detailed description of the present invention is given below with reference to the Examples and Tests relating to production of a dispersion preparation according to the present invention

EXAMPLE 1

To 30 mg of amphotericin B was added an isotonic phosphate buffer solution to maintain a constant volume of 10 ml, after which the solution was dispersed for 60 minutes using an ultrasonic homogenizer (Branson Model 185) while cooling on ice, to obtain a dispersion preparation containing very fine amphotericin B. The resulting preparation produced no precipitation either when allowed to stand or upon centrifugation at 3,000 rpm for 10 minutes. The preparation was then subjected to a conventional method of lyophilization to obtain a dry preparation.

EXAMPLE 2

To 3 g of amphotericin B was added 500 ml of an isotonic phosphate buffer solution, and stirring was effected with a homomixer to make a crude dispersion solutions The crude dispersion solution was then subjected to high pressure dispersion using a Manton-Gauline homogenizer, to obtain a dispersion preparation containing very fine amphotericin B. The resulting preparation produced no precipitation either when allowed to stand or upon centrifugation at 10,000 rpm for 1 hour. The preparation was then subjected to a conventional method of lyophilization to obtain a dry preparation.

EXAMPLE 3

To 30 mg of amphotericin B was added a 0.24M aqueous solution of glycerin to a volume of 10 ml, after which the solution was dispersed for 5 minutes using an ultrasonic homogenizer (Branson Model 185) while cooling on ice, to obtain a dispersion preparation containing very fine amphotericin B. There was no precipitation even after the solution was allowed to stand for half a year. The solution was then subjected to a conventional method of lyophilization to obtain a dry preparation.

EXAMPLE 4

To 2 g of amphotericin B was added 100 ml of a 0.24M aqueous solution of glycerin and stirring was effected with a homomixer to make a crude emulsion solution. The crude emulsion solution was then subjected to high pressure dispersion using a microfluidizer, to obtain a dispersion preparation containing very fine amphotericin B. The resulting preparation produced no precipitation either when allowed to stand or upon centrifugation at 20,000 rpm for 1 hour. The preparation was then subjected to a conventional method of lyophilization to obtain a dry preparation.

EXAMPLE 5

To 1 g of amphotericin B was added 0.1 g of refined egg yolk lecithin as an adjuvant for dispersion, a 10% aqueous solution of maltose was then added to a constant volume of 10 ml, after which the solution was dipsersed for 60 minutes using an ultrasonic homogenizer (Branson Model 185) while cooling on ice, to obtain a dispersion preparation containing very fine amphotericin B. The resulting preparation produced no precipitation either when allowed to stand or upon centrifugation at 3,000 rpm for 10 minutes. The preparation was then subjected to a conventional method of lyophilization to obtain a dry preparation.

EXAMPLE 6

To 0.3 g of amphotericin B and 0.1 g of d imyristoylphosphatidylglycerol was added a 0.24M aqueous solution of glycerin to a constant volume of 10 ml, after which the solution was emulsified for 10 minutes using an ultrasonic homogenizer (Branson Model 185), to obtain a dispersion preparation containing very fine amphotericin B. The resulting preparation produced no precipitation either when allowed to stand or upon centrifugation at 3,000 rpm for 10 minutes. The preparation was then subjected to a conventional method of lyophilization to obtain a dry preparation.

The results of evaluation tests of the characteristics of the dispersion preparations according to the present invention were given below.

In each test, a commercially available amphotericin B preparation, various conventional liposome preparations containing amphotericin B, and a conventional fatty emulsion were used for comparison. The details regarding each of the samples were given below.

Test sample 1: Dispersion preparation according to the present invention obtained in Example 1.

Test sample 2: Dispersion preparation according to the present invention obtained in Example 3.

Control sample 1: Commercially available amphotericin B for injection (Product name: Fungizone (registered trademark), Nihon Squib)

Control sample 2: Dispersion preparation containing amphotericin B, classified as a multilamellar liposome or a lipid composite, prepared according to Document 1 and comprising dimyristoylphosphatidylcholine and dimyristoylphosphatidylglycerol at a molar ratio of 7:3.

Control sample 3: Liposome preparation containing amphotericin B, classified as a small unilamellar liposome, prepared according to Document 1, comprisin gd. imyristoylphosphatidylcholine and dimyristoylp hosphatidylglycerol at a molar ratio of 7:3, and obtained upon ultrasonic treatment.

Control sample 4: Liposome preparation containing amphotericin B, classified as a small unilamellar liposome, prepared according to Document 1, comprising refined egg yolk lecithin, and obtained upon ultrasonic treatment.

Control sample 5: Fatty emulsion containing amphotericin B prepared according to Document 2 and comprising refined soy bean oil and refined egg yolk lecithin.

Test 1: Hemolysis test

The hemolytic effects of Test Sample 1 and Control Sample 1 on purified rat erythrocytes were tested in test tubes, and the results showed considerable hemolysis for Control Sample 1 even at very low concentrations (0.1 µg/ml or greater) of amphotericin B, and absolutely no hemolysis for the test sample at concentrations of 100 times or greater. The dispersion preparation according to the present invention clearly had a much lower hemolytic toxicity than the commercially available preparation.

Test 2: In vivo acute toxicity test

The animals used for experimentation were male ddY mice (body weight approximately 20 g), and the test samples and the control samples were each administered intravenously through the tail vein to evaluate the acute toxicity thereof.

The results were shown in Table 1.

Judgment of the survival rate at 1 hour after administration showed that the test samples all had a very low toxicity. Of the control samples, 2 and 3 showed a lowering of hemolytic-inducing toxicity. However, no alleviation in acute toxicity was observed for Control Samples 1, 4 and 5.

Judgment of the survival rate at 72 hours after administration showed very low toxicities for all of the test samples. However, the control samples all exhibited toxicity, and their nephrotoxicities were considerable in comparison with the test samples. Compared to the liposome preparations and fatty emulsion preparations known in the prior art, the dispersion preparations according to the present invention clearly have a much reduced effect not only of hemolytic toxicity observed immediately after administration, but particularly also of toxicity evaluated at 72 hours after administration which was thought to cause kidney poisoning.

TABLE 1

Toxicity test results

| | LD$_{50}$ (mg/kg) | |
|---|---|---|
| | One hour after administration | 72 hours after administration |
| Test Sample 1 | >50 | >50 |
| Test Sample 2 | >50 | >50 |
| Control Sample 1 | 7 | 4.3 |
| Control Sample 4 | 5.5 | 4.1 |
| Control Sample 5 | 11 | 3.2 |

Test 3: Amount of drug in kidneys (migration to kidneys)

The animals used for experimentation were male SD strain rats (body weight approximately 250 g), and the test samples and the control samples were each administered intravenously through the caudal vein to evaluate the acute toxicity thereof. The dosage was 1 mg/kg in terms of amphotericin B. At 18 hours after administration, the kidneys were extracted and homogenized, after which the concentration of amphotericin B in the kidneys was measured using high performance liquid chromatography (under the conditions as described by H. Hosotsubo, et al., in Antimicrobial Agents and Chemotherapy, 32, 1103–1105, 1988). The results were shown in Table 2.

The concentrations of amphotericin B in the kidneys upon administration of the test samples were all below the measurable limit, but high concentrations of amphotericin B were detected upon administration of the control samples. Compared to the liposome preparations and fatty emulsion preparations known in the prior art, the dispersion preparations according to the present invention clearly produced a considerable improvement in the migration of the drug to the kidneys (a lower rate of migration).

TABLE 2

Amount of amphotericin B migrated to kidneys

| | Concentration in kidneys (μ g/g) |
|---|---|
| Test Sample 1 | Below measurable limit (0.1) |
| Test Sample 2 | Below measurable limit (0.1) |
| Control Sample 1 | 1.4 ± 0.1 |
| Control Sample 2 | 1.3 ± 0.3 |
| Control Sample 5 | 1.5 ± 0.4 |

(average value ± standard deviation, n = 3)

Test 4: Evaluation of kidney functions

The animals used for experimentation were male SD rats (body weight approximately 250 g), and the test samples and the control samples were each administered intravenously through the caudal vein to evaluate the acute toxicity thereof. The dosage was 1 mg/kg in terms of amphotericin B, which was administered a total of 3 times every 24 hours. At 24 hours after the final administration, blood was taken from the jugular vein to obtain the serum. The serum urea nitrogen (BUN) level, used as a kidney function indicator, was measured using a commercially available measuring kit, and the results were shown in Table 3. Physiological saline was administered in the same manner, and the serum obtained and used as a control.

TABLE 3

Biochemical serum evaluation of kidney functions

| | BUN (mg/dl) |
|---|---|
| Control | 14.7 ± 1.7 |
| Test Sample 1 | 15.7 ± 2.3 |
| Test Sample 2 | 14.5 ± 1.4 |
| Control Sample 1 | 29.2 ± 2.6 |
| Control Sample 2 | 29.9 ± 2.1 |
| Control Sample 5 | 37.8 ± 5.4 |

(average value ± standard deviation, n = 3)

The BUN concentrations upon administration of the test samples all showed no contrast with the control, and absolutely no damage to the kidney functions was observed. However, remarkably high BUN concentrations were exhibited upon administration of all the control samples, and damage to the kidney functions was observed. Compared to the liposome preparations and fatty emulsion preparations known in the prior art, the dispersion preparations according to the present invention showed a clear and considerable improvement against kidney function damage.

Test 7: Measurement of particle size

The sizes of the particles of the dispersions of Test Sample 1 and Test Sample 2 were evaluated by laser using a dynamic light scattering particle size analyzer. The results were an average particle size of 55 nm for Test Sample 1, with no particles with a size of 1 μm or greater. The average particle size of Test Sample 2 was 2.5 μm.

Test 8: In vitro antifungal test

Candida cells (Candida albicans) cells were cultured in Sabourand's medium, and the test samples and control samples were each added to the media to determine the minimum amphotericin B concentration required to prevent growth of the Candida cells, and evaluate the antifungal activity of each sample. As shown in Table 4, all of the samples showed antifungal activity at extremely minute concentrations of amphotericin B, and inhibited growth of the Candida cells. The dispersion preparations according to the present invention show absolutely no adverse effects on the antifungal activity exhibited by amphotericin B itself, and thus were an effective and safe method of treatment.

TABLE 4

Antifungal activity (in vitro)

| | Minimum effective concentration (μ g/ml) |
|---|---|
| Test Sample 1 | 0.08 or lower |
| Test Sample 2 | 0.22 or lower |
| Control Sample 1 | 0.20 or lower |
| Control Sample 3 | 0.14 or lower |

We claim:

1. A liquid dispersion suspension consisting essentially of amphotericin B having a particle size of approximately 1 μm or less, persistently dispersed and suspended in water.

2. A dispersion suspension according to claim 1 wherein the water contains a physiologically acceptable saline material.

3. A dispersion suspension according to claim 1 which has been sterilized.

4. A pharmaceutical composition useful for the treatment of a fungal infection or a viral infection in a human or an animal which comprises a liquid dispersion suspension consisting essentially of a therapeutically effective amount of amphotericin B having a particle size of approximately 1 μm or less, persistently dispersed and suspended in water.

5. A dispersion suspension according to claim 4 wherein the water contains a physiologically acceptable saline material.

6. A composition according to claim 4 which contains amphotericin B having a particle size in the range of 0.005 to 1 μm.

7. A composition according to claim 4 in a form suitable for intraarterial, intramuscular, intraspinal or subcutaneous administration.

8. A composition according to claim 4 in parenteral administration form.

9. A composition according to claim 8 in intravenous administration form.

10. A composition according to claim 4 in eyedrop form, nasal drop form, in oral administration form, in inhalant administration form, in the form of a bladder infusion, or in suppository form.

11. A method of treating a fungal or viral infection in a human or an animal which comprises administering to a human or animal in need thereof a composition comprising a liquid dispersion suspension consisting essentially of a therapeutically effective amount of amphotericin B having a particle size of approximately 1 μm or less, until amelioration of the condition occurs.

12. A method according to claim 11 wherein amphotericin B having a particle size in the range of 0.005 to 1 μm is administered.

13. A method according to claim 11 wherein the administration is intraarterially, intramuscularly, intraspinally or subcutaneously.

14. A method according to claim 11 wherein the administration is parenteral.

15. A method according to claim 11 wherein the administration is intravenous.

16. A method according to claim 11 wherein the administration is by eyedrops, nasal drops, orally, inhalant, by bladder infusion, or by suppository.

* * * * *